United States Patent
Agassi et al.

(10) Patent No.: US 10,607,728 B2
(45) Date of Patent: Mar. 31, 2020

(54) ALERT OPTIMIZER

(71) Applicant: CERNER INNOVATION, INC., Kansas City, KS (US)

(72) Inventors: Natalee Agassi, Blue Bell, PA (US); Emin Agassi, Blue Bell, PA (US); Jay Kim, Princeton, NJ (US); John Haley, Chester Springs, PA (US)

(73) Assignee: CERNER INNOVATION, INC., Kansas City, KS (US)

(*) Notice: Subject to any disclaimer, the term of this patent is extended or adjusted under 35 U.S.C. 154(b) by 560 days.

(21) Appl. No.: 14/875,800

(22) Filed: Oct. 6, 2015

(65) Prior Publication Data
US 2017/0098037 A1 Apr. 6, 2017

(51) Int. Cl.
*G16H 10/60* (2018.01)

(52) U.S. Cl.
CPC .............. *G16H 10/60* (2018.01); *Y02A 90/26* (2018.01)

(58) Field of Classification Search
CPC ....... G06F 19/30; G06F 19/34; G08B 25/001; G16H 10/60; Y02A 90/26
See application file for complete search history.

(56) References Cited

U.S. PATENT DOCUMENTS

| | | | |
|---|---|---|---|
| 4,237,344 A | 12/1980 | Moore | |
| 5,319,355 A | 6/1994 | Russek | |
| 5,319,363 A | 6/1994 | Welch et al. | |
| 5,534,851 A | 7/1996 | Russek | |
| 5,942,986 A | 8/1999 | Shabot et al. | |
| 5,999,846 A | 12/1999 | Pardey et al. | |
| 6,754,516 B2 | 6/2004 | Mannheimer | |
| 6,804,656 B1 | 10/2004 | Rosenfeld et al. | |
| 6,928,370 B2 | 8/2005 | Anuzis et al. | |
| 7,035,622 B2 | 4/2006 | Pappalardo et al. | |
| 7,035,623 B2 | 4/2006 | Pappalardo et al. | |
| 7,090,053 B2 | 8/2006 | Bothwell et al. | |
| 7,123,950 B2 | 10/2006 | Mannheimer | |
| 7,215,945 B2 | 5/2007 | Pappalardo et al. | |
| 7,224,281 B2 | 5/2007 | Santoso et al. | |
| 7,225,408 B2 | 5/2007 | O'Rourke | |
| 7,249,036 B2 | 7/2007 | Bayne | |
| 7,256,708 B2 | 8/2007 | Rosenfeld et al. | |
| 7,307,543 B2 | 12/2007 | Rosenfeld et al. | |
| 7,315,825 B2 | 1/2008 | Rosenfeld et al. | |
| 7,321,862 B2 | 1/2008 | Rosenfeld et al. | |
| D577,734 S | 9/2008 | Ryu et al. | |
| 7,430,692 B2 | 9/2008 | White et al. | |
| 7,454,359 B2 | 11/2008 | Rosenfeld et al. | |
| 7,475,019 B2 | 1/2009 | Rosenfeld et al. | |
| D599,812 S | 9/2009 | Hirsch | |

(Continued)

OTHER PUBLICATIONS

First Action Interview Pilot Program Pre-Interview Communication dated Jun. 30, 2017 in U.S. Appl. No. 15/131,231, 15 pages.

(Continued)

*Primary Examiner* — Neal Sereboff
(74) *Attorney, Agent, or Firm* — Shook, Hardy & Bacon L.L.P.

(57) ABSTRACT

An alert optimizer subsystem for a HIT system modifies, reconciles, and/or prioritizes candidate clinical alerts. The optimized alerts may be filtered, prioritized, enriched, and/or formatted so that the alerts are more relevant and/or more actionable for a system user.

15 Claims, 4 Drawing Sheets

(56) References Cited

U.S. PATENT DOCUMENTS

| | | |
|---|---|---|
| D599,813 S | 9/2009 | Hirsch |
| D607,004 S | 12/2009 | Kordus et al. |
| D625,317 S | 10/2010 | Jewitt et al. |
| D631,891 S | 2/2011 | Vance et al. |
| D640,276 S | 6/2011 | Woo |
| 7,981,032 B2 | 7/2011 | Santoso et al. |
| 8,015,030 B2 | 9/2011 | Brown |
| 8,092,380 B2 | 1/2012 | Rothman et al. |
| 8,100,829 B2 | 1/2012 | Rothman et al. |
| 8,122,006 B2 | 2/2012 | de Castro Alves et al. |
| 8,160,895 B2 | 4/2012 | Schmitt et al. |
| 8,165,893 B1 | 4/2012 | Goldberg et al. |
| 8,170,887 B2 | 5/2012 | Rosenfeld et al. |
| 8,175,895 B2 | 5/2012 | Rosenfeld et al. |
| D662,507 S | 6/2012 | Mori et al. |
| D665,399 S | 8/2012 | Carpenter et al. |
| 8,332,017 B2 | 12/2012 | Tarassenko et al. |
| 8,355,925 B2 | 1/2013 | Rothman et al. |
| 8,374,988 B2 | 2/2013 | Gawlick |
| 8,401,606 B2 | 3/2013 | Mannheimer |
| 8,401,607 B2 | 3/2013 | Mannheimer |
| 8,403,847 B2 | 3/2013 | Rothman et al. |
| 8,416,085 B2 | 4/2013 | Gawlick |
| 8,417,233 B2 | 4/2013 | Woloshyn |
| 8,417,662 B2 | 4/2013 | Gawlick |
| D682,294 S | 5/2013 | Kanalakis, Jr. et al. |
| D682,844 S | 5/2013 | Friedlander et al. |
| D682,858 S | 5/2013 | Frijlink |
| 8,451,101 B2 | 5/2013 | Somasundaram et al. |
| 8,454,506 B2 | 6/2013 | Rothman et al. |
| D686,221 S | 7/2013 | Brinda et al. |
| 8,543,534 B2 | 9/2013 | Alves et al. |
| D695,773 S | 12/2013 | Tagliabue et al. |
| D696,682 S | 12/2013 | Kim et al. |
| 8,615,291 B2 | 12/2013 | Moorman et al. |
| D700,914 S | 3/2014 | Jin et al. |
| D701,221 S | 3/2014 | Ahmed et al. |
| D705,239 S | 5/2014 | Thompson et al. |
| 8,775,196 B2 | 7/2014 | Simpson et al. |
| 8,838,196 B2 | 9/2014 | Mannheimer |
| 8,842,001 B2 | 9/2014 | Gilham et al. |
| D714,817 S | 10/2014 | Lee |
| D715,820 S | 10/2014 | Rebstock |
| D717,808 S | 11/2014 | Tsuru et al. |
| 8,886,663 B2 | 11/2014 | Gainsboro et al. |
| 8,886,792 B2 | 11/2014 | Biondi et al. |
| D719,577 S | 12/2014 | Tsuru et al. |
| D720,766 S | 1/2015 | Mandal et al. |
| 8,948,734 B2 | 2/2015 | Vaglio et al. |
| D733,175 S | 6/2015 | Bae |
| 9,052,809 B2 | 6/2015 | Vesto |
| D734,349 S | 7/2015 | Amin et al. |
| D734,350 S | 7/2015 | Inose et al. |
| D736,789 S | 8/2015 | Tursi et al. |
| 9,159,313 B2 | 10/2015 | Saeki et al. |
| D742,909 S | 11/2015 | Lee et al. |
| 9,185,202 B2 | 11/2015 | Herbst et al. |
| D747,343 S | 1/2016 | Brinda et al. |
| D751,097 S | 3/2016 | Sarafa et al. |
| D752,604 S | 3/2016 | Zhang |
| D752,614 S | 3/2016 | Kwon et al. |
| 9,280,637 B2 | 3/2016 | Vaglio et al. |
| D753,165 S | 4/2016 | Watson |
| D753,707 S | 4/2016 | Yang |
| D754,176 S | 4/2016 | Kim |
| D757,771 S | 5/2016 | Drozd et al. |
| D757,778 S | 5/2016 | Lemay |
| D758,386 S | 6/2016 | Zhang |
| D758,400 S | 6/2016 | Chang et al. |
| D759,687 S | 6/2016 | Chang et al. |
| D760,738 S | 7/2016 | Scalisi et al. |
| 9,400,874 B2 | 7/2016 | Powell et al. |
| D762,676 S | 8/2016 | Lim |
| D763,290 S | 8/2016 | Gupta et al. |
| D763,881 S | 8/2016 | Smith et al. |
| D763,882 S | 8/2016 | Liang |
| D764,511 S | 8/2016 | Han et al. |
| D765,110 S | 8/2016 | Liang |
| D766,294 S | 9/2016 | Smith |
| D767,605 S | 9/2016 | Mensinger et al. |
| 9,449,355 B2 | 9/2016 | Kozicki et al. |
| D770,491 S | 11/2016 | Jung |
| D771,667 S | 11/2016 | Woo |
| D771,670 S | 11/2016 | Chan et al. |
| D772,259 S | 11/2016 | Pahwa et al. |
| D775,167 S | 12/2016 | Vazquez |
| D777,184 S | 1/2017 | Yang et al. |
| D777,758 S | 1/2017 | Kisselev et al. |
| D778,929 S | 2/2017 | Mensinger et al. |
| D779,517 S | 2/2017 | Pierson et al. |
| D780,191 S | 2/2017 | Kelley |
| 9,582,978 B2 | 2/2017 | Herbst et al. |
| D781,315 S | 3/2017 | Wang |
| D784,384 S | 4/2017 | Hong et al. |
| D785,003 S | 4/2017 | Yun et al. |
| D785,008 S | 4/2017 | Lim et al. |
| D785,009 S | 4/2017 | Lim et al. |
| D785,012 S | 4/2017 | Jou |
| D785,029 S | 4/2017 | Gedrich et al. |
| 9,626,479 B2 | 4/2017 | Zaleski |
| 9,659,482 B2 | 5/2017 | Yang et al. |
| D789,947 S | 6/2017 | Sun |
| D789,949 S | 6/2017 | Sun |
| 9,706,966 B2 | 7/2017 | Colman et al. |
| 9,747,778 B2 | 8/2017 | Mukherji et al. |
| D801,373 S | 10/2017 | Vaglio et al. |
| 9,805,573 B2 | 10/2017 | Herbst et al. |
| 9,836,940 B2 | 12/2017 | Herbst et al. |
| 9,881,475 B2 | 1/2018 | Herbst et al. |
| 9,911,300 B2 | 3/2018 | Herbst et al. |
| 9,924,908 B2 | 3/2018 | Hubert et al. |
| 2002/0040282 A1* | 4/2002 | Bailey ............... G06F 19/3456 702/188 |
| 2002/0062230 A1* | 5/2002 | Morag ............... G06F 19/324 705/3 |
| 2003/0163789 A1 | 8/2003 | Blomquist |
| 2003/0191730 A1* | 10/2003 | Adkins ............... G06N 5/04 706/47 |
| 2004/0073453 A1 | 4/2004 | Nenov et al. |
| 2004/0172222 A1 | 9/2004 | Simpson et al. |
| 2005/0065817 A1 | 3/2005 | Mihai et al. |
| 2005/0146431 A1 | 7/2005 | Hastings et al. |
| 2005/0151640 A1 | 7/2005 | Hastings |
| 2006/0049936 A1 | 3/2006 | Collins et al. |
| 2006/0161457 A1* | 7/2006 | Rapaport ............... G06Q 10/10 705/2 |
| 2007/0239488 A1 | 10/2007 | DeRosso |
| 2008/0021709 A1 | 1/2008 | Greer |
| 2008/0027288 A1 | 1/2008 | Renz |
| 2008/0074951 A1 | 3/2008 | Hubicki |
| 2009/0048868 A1 | 2/2009 | Portnoy et al. |
| 2010/0001838 A1 | 1/2010 | Miodownik et al. |
| 2010/0123587 A1 | 5/2010 | Walls |
| 2010/0137693 A1 | 6/2010 | Porras et al. |
| 2010/0223071 A1 | 9/2010 | Kland et al. |
| 2011/0001605 A1 | 1/2011 | Kiani et al. |
| 2011/0054946 A1 | 3/2011 | Coulter et al. |
| 2011/0105979 A1* | 5/2011 | Schlaeper ............ A61B 5/0002 604/5.01 |
| 2011/0106560 A1 | 5/2011 | Eaton, Jr. et al. |
| 2011/0196306 A1 | 8/2011 | De La Huerga |
| 2011/0208816 A1 | 8/2011 | Chavez |
| 2011/0276396 A1* | 11/2011 | Rathod ............... G06Q 10/00 705/14.49 |
| 2011/0295621 A1* | 12/2011 | Farooq ............... G06Q 10/10 705/3 |
| 2012/0075103 A1 | 3/2012 | Powell et al. |
| 2012/0101847 A1 | 4/2012 | Johnson et al. |
| 2012/0169467 A1 | 7/2012 | Condra |
| 2012/0278104 A1 | 11/2012 | Traughber et al. |
| 2012/0284040 A1 | 11/2012 | Dupin |
| 2013/0009783 A1 | 1/2013 | Tran |
| 2013/0049950 A1 | 2/2013 | Wohlert |
| 2013/0065569 A1 | 3/2013 | Leipzig et al. |

(56) References Cited

U.S. PATENT DOCUMENTS

| | | | |
|---|---|---|---|
| 2013/0085765 A1 | 4/2013 | Tuchinda et al. | |
| 2013/0085798 A1 | 4/2013 | Spatola et al. | |
| 2013/0096953 A1 | 4/2013 | Beverly et al. | |
| 2013/0103768 A1 | 4/2013 | Freebeck | |
| 2013/0104077 A1 | 4/2013 | Felt | |
| 2013/0162424 A1 | 6/2013 | Treacy | |
| 2013/0183923 A1 | 7/2013 | Brackett et al. | |
| 2013/0297348 A1* | 11/2013 | Cardoza | G16H 10/60 705/3 |
| 2014/0039351 A1 | 2/2014 | Mix et al. | |
| 2014/0051399 A1 | 2/2014 | Walker et al. | |
| 2014/0070939 A1 | 3/2014 | Halverson et al. | |
| 2014/0085080 A1 | 3/2014 | Carnes | |
| 2014/0097961 A1 | 4/2014 | Vaglio et al. | |
| 2014/0099929 A1 | 4/2014 | Vaglio et al. | |
| 2014/0100873 A1 | 4/2014 | Vaglio et al. | |
| 2014/0132413 A1 | 5/2014 | Fox et al. | |
| 2014/0172996 A1* | 6/2014 | Deeter | H04L 51/24 709/206 |
| 2014/0184408 A1 | 7/2014 | Herbst et al. | |
| 2014/0337442 A1* | 11/2014 | Zhuang | H04L 51/066 709/206 |
| 2014/0358585 A1* | 12/2014 | Reiner | G06F 16/219 705/3 |
| 2015/0081339 A1 | 3/2015 | Vaglio et al. | |
| 2015/0137968 A1* | 5/2015 | Rusin | G08B 25/001 340/506 |
| 2015/0148617 A1* | 5/2015 | Friedman | A61B 5/7275 600/301 |
| 2015/0254957 A1 | 9/2015 | Wilson et al. | |
| 2016/0027277 A1 | 1/2016 | Herbst et al. | |
| 2016/0110040 A1 | 4/2016 | Vaglio et al. | |
| 2016/0360160 A1 | 12/2016 | Eizenberg | |
| 2017/0024091 A1 | 1/2017 | Hosier, Jr. | |
| 2017/0032093 A1 | 2/2017 | Norton et al. | |
| 2017/0098037 A1 | 4/2017 | Agassi et al. | |
| 2017/0109018 A1 | 4/2017 | Vaglio et al. | |
| 2017/0109989 A1 | 4/2017 | Herbst et al. | |
| 2017/0193801 A1 | 7/2017 | Bala et al. | |
| 2017/0265819 A1 | 9/2017 | Colman et al. | |
| 2017/0287300 A1 | 10/2017 | Herbst et al. | |
| 2017/0352237 A1 | 12/2017 | Herbst et al. | |
| 2017/0352238 A1 | 12/2017 | Herbst et al. | |
| 2018/0102036 A1 | 4/2018 | Herbst et al. | |
| 2018/0110477 A1 | 4/2018 | Collins et al. | |
| 2018/0144598 A1 | 5/2018 | Herbst et al. | |
| 2018/0153455 A1 | 6/2018 | Guazzi et al. | |
| 2018/0315428 A1 | 11/2018 | Johnson et al. | |
| 2019/0066841 A1 | 2/2019 | Bala et al. | |
| 2019/0244506 A1 | 8/2019 | Herbst et al. | |
| 2019/0294318 A1 | 9/2019 | Vaglio et al. | |

OTHER PUBLICATIONS

Riano et al., "MPM: A Knowledge-based functional model of medical practice", Journal of Biomedical Informatics 46 (2013) 379-387.
Non-Final Office Action dated Jan. 30, 2014 in U.S. Appl. No. 13/711,217, 8 pages.
Final Office Action dated Jun. 19, 2014 in U.S. Appl. No. 13/711,217, 8 pages.
Final Office Action dated Jul. 7, 2014 in U.S. Appl. No. 13/711,177, 12 pages.
First Action Interview Pre-Interview Communication dated Sep. 25, 2014 in U.S. Appl. No. 13/711,206, 5 pages.
Notice of Allowance dated Sep. 29, 2014 in U.S. Appl. No. 13/711,217, 7 pages.
First Action Interview Preinterview Communication dated Dec. 4, 2014 in U.S. Appl. No. 13/731,191, 5 pages.
Final Office Action dated Feb. 20, 2015 in U.S. Appl. No. 13/711,177, 11 pages.
Non-Final Office Action dated Mar. 17, 2015 in U.S. Appl. No. 13/711,206, 8 pages.
First Action Interview Office Action dated Jun. 3, 2015 in U.S. Appl. No. 13/731,191, 4 pages.
Non-Final Office Action dated Jul. 8, 2015 in U.S. Appl. No. 13/711,177, 5 pages.
Final Office Action dated Oct. 2, 2015 in U.S. Appl. No. 13/711,206, 15 pages.
Notice of Allowance dated Oct. 29, 2015 in U.S. Appl. No. 13/711,177, 9 pages.
Non-Final Office Action dated Feb. 25, 2016 in U.S. Appl. No. 13/711,206, 17 pages.
Final Office Action dated Nov. 3, 2016 in U.S. Appl. No. 13/711,206, 20 pages.
Non-Final Office Action dated Sep. 8, 2016 in U.S. Appl. No. 14/877,808, 7 pages.
Notice of Allowance dated Jan. 5, 2017 in U.S. Appl. No. 14/877,808, 5 pages.
Non-Final Office Action dated Mar. 23, 2017 in U.S. Appl. No. 13/711,206, 10 pages.
First Action Interview Pre-Interview Communication dated Apr. 13, 2017 in U.S. Appl. No. 14/551,555, 5 pages.
First Action Interview Pre-Interview Communication dated Jun. 30, 2017 in U.S. Appl. No. 15/131,231, 5 pages.
Non-Final Office Action dated Jul. 13, 2017 in U.S. Appl. No. 29/602,910, 14 pages.
Notice of Allowance dated Jul. 19, 2017 in U.S. Appl. No. 29/602,800, 15 pages.
Final Office Action dated Jul. 27, 2017 in U.S. Appl. No. 13/711,206, 14 pages.
First Action Interview Pre-Interview Communication dated Aug. 17, 2017 in U.S. Appl. No. 15/392,926, 5 pages.
Non-Final Office Action dated Sep. 21, 2017 in U.S. Appl. No. 15/630,617, 7 pages.
Notice of Allowance dated Sep. 28, 2017 in U.S. Appl. No. 15/392,926, 9 pages.
Notice of Allowance dated Oct. 30, 2017 in U.S. Appl. No. 15/630,617, 7 pages.
First Action Interview Pre-Interview Communication dated Nov. 15, 2017 in U.S. Appl. No. 15/684,565, 5 pages.
First Action Interview Pre-Interview Communication dated Nov. 30, 2017 in U.S. Appl. No. 15/684,563, 5 pages.
Notice of Allowance dated Dec. 19, 2017 in U.S. Appl. No. 15/684,565, 9 pages.
Notice of Allowance dated Jan. 10, 2018 in U.S. Appl. No. 15/684,563, 5 pages.
Final Office Action dated Jan. 23, 2018 in U.S. Appl. No. 14/551,555, 22 pages.
Notice of Allowance dated Jan. 30, 2018 in U.S. Appl. No. 15/131,231, 7 pages.
Final Office Action dated Mar. 2, 2018 in U.S Appl. No. 29/602,910, 13 pages.
Notice of Allowance dated Apr. 25, 2018 in U.S. Appl. No. 15/131,231, 5 pages.
Clinical Workflow Solutions Extension HealthAlert brochure published by NEC Corporation Sep. 17, 2012.
Press Release by Extension Healthcare entitled: "Arc Solutions and Extension, Inc. Announce New Collaboration Software Solutions, Specifically Designed for the Healthcare Sector", Jan. 7, 2010.
Extension Mobile for Enterprise Healthcare Organizations Now Available on Apple iPhone and iPod Touch via Apple AppStore, http://www.extensionhealthcare.com, Extension, Inc., Fort Wayne, IN, Jan. 10, 2011, 2 pages.
Extension, Inc. and AeroScout Partner to Deliver Solutions for Healthcare RTLS and VoIP, http://www.extensionhealthcare.com, Extension, Inc., Fort Wayne, IN, Feb. 19, 2010, 2 pages.
Extension, Inc. Launches New Interactive Communications Solution, http://www.extensionhealthcare.com, Extension, Inc., Fort Wayne, IN, May 25, 2011, 3 pages.
The American Hospital Association Endorses the Extension Healthid smart card system, http://www.news-medical.net, Published Aug. 21, 2009, 2 pages.
How to Set Up Zoom on Android, http://blog.recovery-android.com/set-up-zoom-in-android/, Jan. 14, 2016, 3 pages.

(56) References Cited

OTHER PUBLICATIONS

ExDialer Dialer & Contacts, Modoohut Communication, Android Apps on Google Play, Accessed Apr. 24, 2017 at: https://playgoogle.com/store/apps/details?id=com.modoohut.dialer&hl=en, 3 pages.

How to download Skype app on Android and do Voice and video chat, Oct. 29, 2012, 5 pages. Available at: http://www.howto-connect.com/how-to-download-skype-app-on-android-and-do-voice-and-video-chat/.

Contactive—A Caller ID App that Showcases Android's Openess, 3 pages. Accessed Apr. 24, 2017 at: http://techdomino.com/contactive-a-caller-id-app-that-showcases-androids-openess/.

Review: Our Favourite Effective Contact Managers, Contaker Blog, 6 pages. Accessed Apr. 24, 2017 at: http://blog.contaker.com/?p=61.

How to Design an iPhone App in Photoshop, by Tony Thomas, dated Oct. 26, 2011, medialoot.com [online], [retrieved Jul. 3, 2017], Available from Internet URL:https://medialoot.com/blog/how-to-design-an-iphone-app-in-photoshop/.

Find and replace pop-up window, by Jerome Detraz, dated Jul. 17, 2013, sketchappsource.com [online], [retrieved Jul. 3, 2017]. Available from internet <URL: https://web.archive.org/web/2 13071 7090053/https:/ /www.sketchappsources.com/free-source/190-find-replace-pop-up-window.html.

How to create a cool and usable CSS3 search box, dated Feb. 18, 2011, catalin.red [online], [retrieved Feb. 23, 2018]. Retrieved from internet <URL:https://catalin.red/how-to-create-a-cool-and-usable-css3-search-box/> (Year: 2011).

How to Add Search Bar in Table View, by Simon NG, dated Jul. 8, 2012, appcoda.com [online], [retrieved Feb. 23, 2018]. Retrieved from internet <URL:https://www.appcoda.com/how-to-add-search-bar-uitableview/> (Year: 2012).

First Action Interview Office Action dated Aug. 9, 2017 in U.S. Appl. No. 14/551,555, 8 pages.

Non-Final Office Action received for U.S. Appl. No. 14/551,555, dated Oct. 10, 2018, 29 pages.

Non-Final Office Action received for U.S. Appl. No. 15/290,443, dated Aug. 15, 2018, 7 pages.

Non-Final Office Action received for U.S. Appl. No. 15/837,856, dated Jul. 25, 2018, 7 pages.

Pre-Interview First Office Action received for U.S. Appl. No. 14/983,685, dated Jul. 6, 2018, 9 pages.

Notice of Allowance received for U.S. Appl. No. 14/983,685, dated Mar. 12, 2019, 10 pages.

Final Office Action received for U.S. Appl. No. 14/551,555, dated May 16, 2019, 21 pages.

Non-Final Office Action received for U.S. Appl. No. 16/179,096, dated Sep. 3, 2019, 7 pages.

\* cited by examiner

ALERT OPTIMIZER

TECHNICAL FIELD

The present disclosure relates generally to Health Information Technology (HIT) systems, and more specifically to a HIT subsystem for managing healthcare-related alerts.

BACKGROUND

One potential advantage of using Electronic Health Records (EHRs) and other Health Information Technology (HIT) in clinical settings is the ability to quickly process large volumes of data from diverse sources and identify potential problems. Many HIT systems include, for example, Clinical Order Entry (COE) subsystems, which allow a clinician to order tests or medications for a patient. Those HIT systems may also include Clinical Conflict Check (CCC) subsystems, which acquire relevant data from within the HIT system and alert the clinician to inconsistencies or potential problems. For example, CCCs may alert clinicians to duplicate orders, potential undesirable drug interactions, incongruent data entry (e.g., observations related to the tonsils in a patient who has had a tonsillectomy) and other facially problematic data or order entries. CCCs may also alert clinicians to items of information like known patient allergies or risk factors that may influence the course of a patient encounter or a treatment plan.

The alerts are meant to improve healthcare efficiency and patient outcomes. Identifying duplicate orders, for example, could avoid the expense and delay associated with repeating a recently completed medical test, or avoid an accidental drug overdose. As another example, identifying possible undesirable drug interactions may prevent adverse events, particularly when a patient is taking many medications, or is taking medications prescribed by two or more clinicians. Unfortunately, empirical data suggests that such alerts are often ignored. In some systems, over 95% of medical order alerts are overridden or ignored. While this suggests that a small percentage of medical order alerts are valid and acted upon to prevent potential problems, the proportion of alerts that are acted upon suggests that conventional alerts are often not useful.

There remains a need for a clinical HIT system that provides meaningful, actionable alerts.

BRIEF SUMMARY

This brief summary is provided as a general overview of the more detailed disclosure which follows. It is not intended to identify key or essential elements of the disclosure, or to define the claim terms in isolation from the remainder of the disclosure, including the drawings.

The disclosure generally relates to methods and systems for processing and handling alerts for clinicians in a Health Information Technology (HIT) system. A Clinical Conflict Check (CCC) system may be used with a Clinical Order Entry (COE) system to identify possible problems or undesired outcomes before a clinical order is fulfilled (e.g., before a medication is delivered). An Alert Optimizer may filter, prioritize, enrich and/or format candidate alerts from a CCC system. The Alert Optimizer may reconcile candidate clinical alerts against one another, against a history of responses to prior alerts, against the patient's EHR, against a medical knowledge model, against prior patient clinical choices, and/or against patient care directives. Optimizing and/or reconciling candidate clinical alerts may result in optimized and/or reconciled alerts which are more relevant and more important, on the whole, than the candidate alerts were.

Additional objects, advantages, and novel features of the disclosure will be set forth in part in the description which follows, and in part will become apparent to those skilled in the art upon examination of the following, or may be learned by practice of the disclosure.

BRIEF DESCRIPTION OF THE SEVERAL VIEWS OF THE DRAWING

The following disclosure makes reference to the attached drawing figures, wherein.

DETAILED DESCRIPTION

Figure 1:
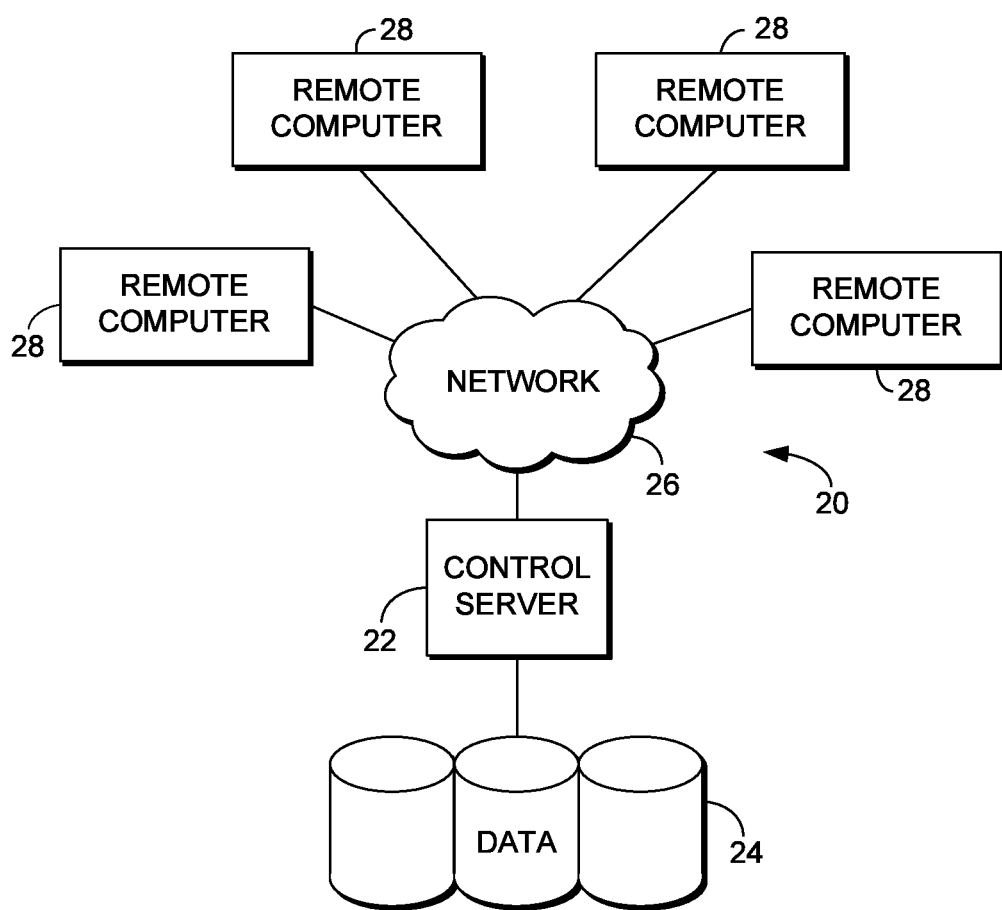
FIG. 1 is a block diagram depicting an exemplary computing environment suitable for use in implementing embodiments of the present invention.

If over 95% of alerts are ignored or overridden, not only are a low percentage of the alerts effective in avoiding a potential problem, but a high percentage of alerts are consuming processing capacity and clinician time with no evident benefit. Further, even a diligent clinician who is accustomed to overriding or ignoring alerts most of the time may habitually ignore an alert of great clinical significance. Relatively high proportions of irrelevant and/or insignificant alerts may pose an ergonomic problem in that the software may condition users to ignore alerts. Some care-delivery organizations have resorted to creating and publishing lists of, e.g., drug interactions, that most warrant a clinician's attention. In these systems, a clinician may consult a separate, sometimes hard copy, list of alerts which should not be ignored. In other systems, the HIT alerts are disabled altogether, relying instead on other systems and/or personnel to identify potential problems. For example, if HIT alerts are disabled, a care delivery organization may rely on pharmacy personnel to identify potential adverse drug reactions, including potential adverse drug interactions. This is not ideal. Among the aspirational benefits of the HIT alert systems was the ability to identify potential problems that might be missed by human clinicians, e.g., because a clinician might be unaware of a potential drug interaction between drugs that are not routinely prescribed together, or because of complicated or lengthy medical histories that might make it difficult to identify and assess latent risks.

In some aspects, this disclosure relates to an alert optimizer which organizes, prioritizes, and/or enhances alerts. In some aspects, the alert optimizer may be built-in to a CCC. In some aspects, the alert optimizer may intercept alerts from a pre-existing CCC and modify how the alerts are presented to a system user. In some aspects, these changes in alert processing and handling may make the alerts more relevant and more actionable, thereby enabling the intended improvements in patient care delivery. In some aspects, these changes in alert processing and handling may avoid the ergonomic issues posed by a system where clinicians ignore alerts more often than not. In some aspects, these changes in alert processing and handling may conserve processor resources, including Random Access Memory (RAM) and processing capacity, by reducing the number of alerts presented to a user and, correspondingly, the number of responses to alerts that must be received and processed. When the alert optimizer resides on a computing system remote from the user access point, these changes may reduce the network bandwidth and/or latency for transmitting alerts and responses to alerts between the alert optimizer and the user access point. In some aspects, these changes in alert processing and handling may reduce the amount of clinician time spent reviewing alerts that are irrelevant or unimportant. In some aspects, these changes in alert processing and handling may reduce the opportunities for alert "loops" and other conflicts.

As used herein, "HIT" or "Health Information Technology" system refers to a computer system that provides centralized records related to clinical aspects of a patient's healthcare. The HIT may include records entered directly into an Electronic Health Record (EHR) for a patient, or may include records added to the EHR, as by transcription, scanning, etc., after a patient care encounter, such as an appointment with a clinician. Entries in an EHR may be made by a human system user or may be made by data transfer from, e.g., medical devices and/or other computing systems. EHR entries made by a human system user may be made by a clinician, by an administrative professional, such as a clerk or transcriptionist, by a patient or a non-clinical care provider for the patient, or combinations thereof. Some HIT systems may be significantly more sophisticated, providing, for example, integrated systems related to insurance, billing, scheduling, staffing, and other aspects of managing a healthcare delivery organization.

As used herein, a "healthcare delivery organization" includes any clinicians with shared access to the HIT system, and may include independent healthcare providers, hospitals, outpatient care centers, and the like. For privacy, security, usability of the user interface, and/or other reasons, access to different information or user interfaces within the HIT system may vary among different clinicians who have shared access to the HIT system.

As used herein, a "patient encounter" refers to any interaction between a patient and a clinician that might be documented in an EHR. Patient encounters may involve an in-person interaction, or remote "telemedicine" interactions, or remote communications, as when a patient calls or e-mails a clinician to clarify the clinician's instructions, report a change in the patient's condition, or seek health-related advice.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

In some aspects, this disclosure relates to computerized methods, systems, and graphical user interfaces for preserving computer processing capacity and/or network bandwidth and/or computer memory storage capacity in a HIT system. In some aspects this disclosure relates to computerized methods, systems, and graphical user interfaces for improving a human-user interface for clinical alerts in a HIT system. In some aspects, this disclosure relates to computerized methods, systems, and graphical user interfaces for reducing the amount of time clinicians spend reviewing HIT-originated clinical alerts. In some aspects, this disclosure relates to computerized methods, systems, and graphical user interfaces for preventing clinical alert loops.

FIG. 1 depicts an exemplary computing system environment suitable for implementing various aspects of the disclosure. Health Information Technology (HIT) system 20 is merely one example of many feasible system architectures and is not intended to suggest any limitation as to the scope of use or functionality of the system or other aspects of the disclosure. Neither should HIT system 20 be interpreted as having any dependency or requirement relating to any single component or combination of components as illustrated in the exemplary depiction.

With continued reference to FIG. 1, the exemplary HIT system 20 includes a general purpose computing device in the form of a control server 22. Components of the control server 22 may include, without limitation, a processing unit, internal system memory, and a suitable system bus for coupling various system components, including database cluster 24, with the control server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus.

The control server 22 typically includes therein, or has access to, a variety of computer-readable media, for instance, database cluster 24. Computer-readable media can be any available media that may be accessed by control server 22, and includes volatile and nonvolatile media, as well as removable and non-removable media. By way of example, and not limitation, computer-readable media may include computer-storage media and communication media. Computer-storage media may include, without limitation, volatile and nonvolatile media, as well as removable and non-removable media implemented in any method or technology for storage of information, such as computer readable instructions, data structures, program modules, or other data. In this regard, computer-storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 22. Computer-storage media excludes signals per se.

Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer-readable media. The computer-storage media discussed above and illustrated in FIG. 1, including database cluster 24, provide storage of computer readable instructions, data structures, program modules, and other data for the control server 22.

The control server 22 may operate in a computer network 26 using logical connections to one or more remote computers 28. Remote computers 28 may be located at a variety of locations in a medical or research environment, for example, but not limited to, clinical laboratories (e.g., molecular diagnostic laboratories), hospitals and other inpatient settings, veterinary environments, ambulatory settings, medical billing and financial offices, hospital administration settings, home health care environments, and clinicians' offices and the clinician's home or the patient's own home or over the Internet. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, laboratory technologists, genetic counselors, researchers, veterinarians, students, and the like. The remote computers 28 may also be physically located in non-traditional medical care environments so that the entire health care community may be capable of integration on the network. The remote computers 28 may be personal computers, servers, routers, network PCs, peer devices, other common network nodes, or the like, and may include some or all of the elements described above in relation to the control server 22. The devices can be personal digital assistants or other like devices.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the control server 22 may include a modem or other means for establishing communications over the WAN, such as the Internet. In a networked environment, program modules or portions thereof may be stored in the control server 22, in the database cluster 24, or on any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., control server 22 and remote computers 28) may be utilized.

In operation, a user may enter commands and information into the control server 22 or convey the commands and information to the control server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the control server 22. In addition to a monitor, the control server 22 and/or remote computers 28 may include other peripheral output devices, such as speakers and a printer.

Many other internal components of the control server 22 and the remote computers 28 are not shown because such components and their interconnection are well known. Accordingly, additional details concerning the internal construction of the control server 22 and the remote computers 28 are not further disclosed herein.

Methods and systems of embodiments of the present invention may be implemented in a WINDOWS or LINUX operating system, operating in conjunction with an Internet-based delivery system. One of ordinary skill in the art will recognize that the described methods and systems can be implemented in any alternate operating system suitable for supporting the disclosed processing and communications. As contemplated, the methods and systems of embodiments of the present invention may also be implemented on a stand-alone desktop, personal computer, cellular phone, smart phone, PDA, or any other computing device used in a healthcare environment or any of a number of other locations.

Figure 2:
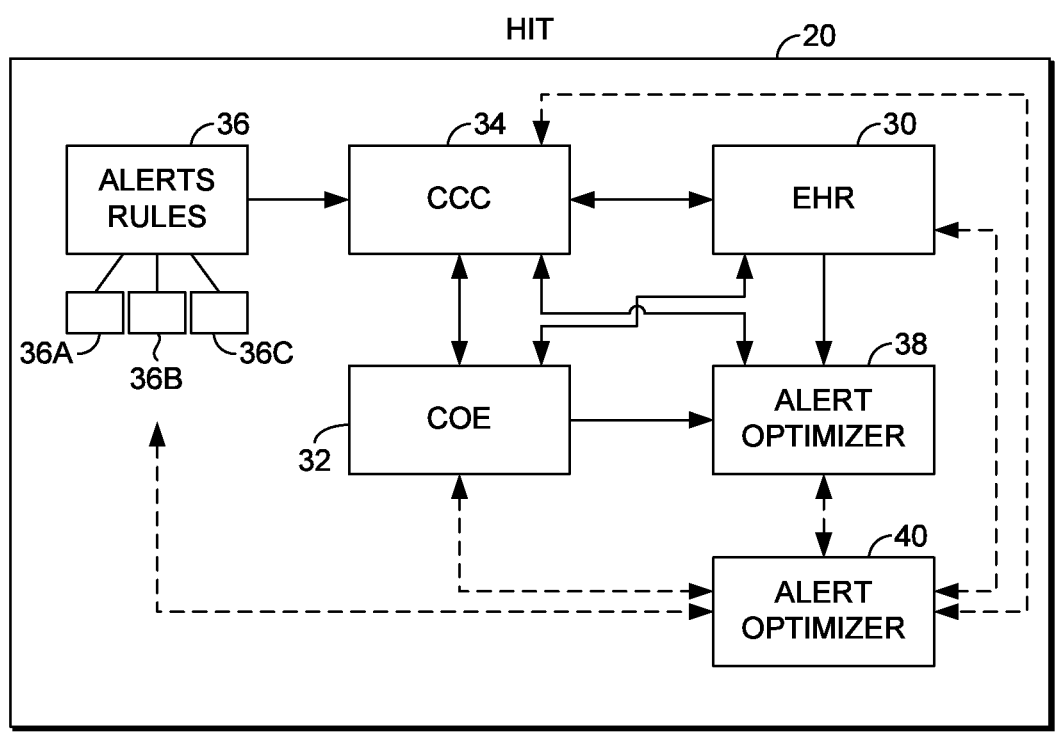
FIG. 2 is a schematic diagram of an exemplary HIT system.

A HIT system 20, as shown in FIG. 2, may comprise a number of subsystems. It should be understood that these subsystems may reside in modular or fully integrated software, and, as mentioned above, may reside on a single computer or one or more subsystems may reside on a networked computer distinct from one or more networked computers storing other subsystems and/or data stores. An EHR subsystem 30 may maintain individual patients' medical records, which may also be called personal health care records, as Electronic Health Records (EHRs). The EHR subsystem 30 may be an electronic file containing documents and/or database entries. The EHR subsystem 30 may also have user interfaces for creating, modifying (including adding to, deleting from, or editing existing records), viewing, searching, excerpting, transferring, archiving, and/or printing records or portions thereof. HIT system 20 may include, as a separate subsystem or as a subsystem of EHR subsystem 30, a Clinical Order Entry (COE) subsystem 32. COE subsystem 32 may allow clinicians to place orders for tests, medications, treatments, and other products, examinations, referrals, or clinical follow-up for a patient. Such orders might include, for example, laboratory tests, drug administration orders, prescriptions for self-administration of controlled medications, prescriptions for home medications, physical therapy, preventative procedures, diagnostic procedures, therapeutic procedures, specialized examinations, requests for review or examination by another clinician, follow-up instructions (e.g., retest after a particular time period or treatment), or combinations thereof. COE Subsystem 32 may include a database into which clinicians may directly or indirectly (e.g., through a graphical user interface and/or web browser) enter orders. COE subsystem 32 may store orders, or may communicate orders for use and/or storage in a separate database, such as a database associated with EHR subsystem 30 or other elements of HIT system 20.

HIT system 20 may include a Clinical Conflict Check (CCC) subsystem 34. CCC subsystem 34 may receive or extract data from the EHR subsystem 30 and/or the COE subsystem 32. CCC subsystem 34 may access alert rules 36, which may be stored on the same computing system as CCC subsystem 34 or on any suitable networked computing device. CCC subsystem 34 may access different versions of alert rules 36 under different circumstances. For example, a physician's office may use a set of alert rules 36a which are accessible by the same HIT system 20 (or components thereof) used by a pharmacy, where the pharmacy uses a separate set of alert rules 36b, and the same HIT system 20 (or components thereof) may be used by an in-patient hospital, where the hospital uses a separate set of alert rules 36c. The CCC subsystem 34 may select the appropriate version of alert rules 36 based on the identity of the clinician, the role of the clinician (e.g., doctor, pharmacist, surgeon, etc.), the location of the services, and/or any other designated criteria.

The CCC subsystem 34 may apply alert rules 36 to data received or extracted from the EHR subsystem 30 and/or the COE subsystem 32 to identify candidate clinical alerts for a given EHR. Candidate clinical alerts may include, as examples, reminders of best practices, seasonal and/or regional healthcare notices (e.g., information related to the flu season, allergy season, Lyme disease, or a local epidemic), policies or recommendations of the healthcare delivery organization, identification of possible errors or omissions in data entry into the patient's EHR, identification of inconsistent information in the EHR, identification of information in the EHR that is inconsistent with a recent clinical order, identification of duplicate clinical orders, identification of possible adverse effects or interactions among various elements of the EHR and/or a recent clinical order, and identification of known or nearly certain adverse effects or interactions (e.g., patient allergies or contraindications).

A variety of approaches may be useful in a CCC subsystem 34, including, without limitation, Markov decision processing; approximate linear programming; natural language extraction solvers (e.g., nCode®), non-linear programming or multi-layer perceptron solvers); fuzzy-neural networks; logistic and linear regression; forward-chaining inference (e.g., data-driven); backward-chaining inference (e.g., goal-driven); inductive inference; genetic algorithm; neural network including with genetic algorithm for training; stochastic; self-organizing Kohenen map; Q-learning; quasi-Newton; gradient; decision trees; lower/higher bond search; constraint satisfaction; Naive Bayes fuzzy; LP-solver including mixed integer multi-variable min/max solvers; Finite State Machine (FSM) and Hierarchical FSM (HFSM); temporal difference reasoning; data mining for classification, clustering, learning and prediction; K-means; support vector machines; K-nearest neighbor classification; Tanimoto distance; C5.0; a priori; EM, simulated annealing, Tabu search, multi-criteria decision making, evolutionary algorithm, and other such solvers. Exemplary CCC subsystems 34 are disclosed in WO 2015/023674A1, which is herein incorporated by reference in its entirety, including related structures and functions.

A plurality of candidate clinical alerts may be generated from a relatively simple patient encounter. For example, a visit to a primary care physician by a generally healthy 50-year old patient may result in new entries into the patient's EHR. A CCC system may generate candidate clinical alerts, for example, recommending a colonoscopy, recommending a flu shot, soliciting laboratory results for bloodwork related to cholesterol and triglyceride levels, identifying a possible interaction between the patient's daily vitamin and an ordered prescription medication, identifying an undesirable increase in Body Mass Index since the patient's last visit, and advising the physician of a prior sensitivity response to latex. More complex medical histories, conditions, and/or patient encounters could generate dozens of candidate clinical alerts.

HIT system 20 may include, as a component of CCC subsystem 34 or as a separate component, Alert Optimizer 38. Alert Optimizer 38 may reconcile candidate clinical alerts. For example, a candidate clinical alert may be generated because the date of the patient encounter is after a particular date in the calendar year associated with the start of flu season, and the EHR does not reflect the administration of a flu shot. However, Alert Optimizer 38 may receive or extract data from EHR subsystem 30 indicating that the patient has consistently declined the flu vaccine over a certain period of time (e.g., 5 years), or that the patient has declined all vaccinations. Alert Optimizer 38 may then filter out the candidate clinical alert reminding the physician to administer or recommend a flu shot.

Alert Optimizer 38 may prioritize candidate clinical alerts. For example, Alert Optimizer 38 may include or connect to a medical knowledge model. Exemplary medical knowledge models are described, for example, in U.S. Pat. No. 8,160,895 to Schmitt, et al.; and Raiño, et al., MPM: A knowledge-based functional model of medical practice, Journal of Biomedical Informatics 46 (2014) 379-387, each of which is hereby incorporated by reference in its entirety. Other models are known in the art and may be used or adapted for use with the concepts of this disclosure. Using the medical knowledge model to extract relevant situational details from the EHR, Alert Optimizer may further use the medical knowledge model to score each candidate clinical alert for likelihood and severity of an adverse event associated with the candidate clinical alert. Returning to the example of the 50-year-old male visiting a primary care physician, as between the candidate clinical alerts for recommending a colonoscopy, recommending a flu shot, soliciting laboratory results for bloodwork related to cholesterol and triglyceride levels, identifying a possible interaction between the patient's daily vitamin and an ordered prescription medication, identifying an undesirable increase in Body Mass Index since the patient's last visit, and advising the physician of a prior sensitivity response to latex, the most urgent of these based on severity of possible adverse event are likely the sensitivity response to latex and the potential drug interaction. The Alert Optimizer 38 may prioritize the latex sensitivity over the potential drug interaction on the basis that this particular patient has a history of latex sensitivity reactions. Alternately, if the potential drug interaction is both likely to occur, even in the absence of an individual history of adverse response, and the result is more severe than the nature of the previously observed sensitivity response, Alert Optimizer 38 may prioritize the alert related to the potential drug interaction.

The alert risk classification used by Alert Optimizer 38 may be generic. For example, Alert Optimizer 38 may use risk classifications based on widely accepted clinical studies and medical treatises. Alert Optimizer 38 may use alert risk classifications customized to a particular practice or institution. For example, a particular physician or hospital may believe from personal or institutional experience that the risk of a particular adverse reaction is somewhat lower or somewhat higher than a generic alert risk classification. That physician or hospital may adjust the alert optimizer used in the physician's office or the hospital or the hospital network to reflect a lower or higher alert risk for an alert for that particular adverse reaction. Alternately, or in addition to, relying on personal experience, a particular physician or hospital or hospital network may be more or less inclined to act upon relatively new clinical data that might not yet be considered widely accepted. That physician or hospital or hospital network may customize alert risk classifications to reflect developing evidence ahead of the adaptation of a generic alert risk classification. One of skill in the art will appreciate that many other adaptations are possible. A particular Alert Optimizer 38 may reference different alert risk classifications for different facilities (e.g., distinguishing between a hospital, an urgent care center, and a primary care center within a hospital network using a shared HIT System 20) or users (e.g., distinguishing between different clinicians within a practice group or department). In a customized alert risk classification, the alert risk classification may or may not correlate directly to the previously observed probability or magnitude of an adverse event.

By filtering candidate clinical alerts, Alert Optimizer 38 can reduce the total number of alerts presented to a clinician for review, saving both clinician time and processing resources for the HIT System 20. Further, the alerts that are presented should be more relevant and more important than the complete set of candidate clinical results. By prioritizing candidate clinical alerts, in addition to or instead of filtering the candidate clinical alerts, Alert Optimizer 38 may present the most clinically significant alerts first, so that even if a plurality of candidate clinical results are identified, a clinician's attention is focused early on the most important and most relevant alerts. In this way, if a clinician experiences "alert fatigue" and is unable to give all of the alerts his or her full attention, those alerts that get the most attention are those most likely to benefit the patient. The Alert Optimizer 38 may be activated automatically by HIT System 20 or a subsystem of HIT System 20. In some embodiments, Alert Optimizer 38 may be activated by a system user. For example, a clinician or other user may be able to select a menu option to activate the Alert Optimizer.

HIT System 20 may further comprise other subsystems 40. Other subsystems 40 may include subsystems related, for example, to insurance, billing, scheduling, staffing, and other aspects of managing a healthcare delivery organization. In some embodiments, other subsystems 40 may receive feedback from and/or forward information to other aspects of HIT System 20. For example, in addition to clinical alerts, CCC subsystem 34 may communicate with other subsystems 40 to provide administrative alerts. For example, CCC subsystem 34 may alert a clinician if an ordered treatment is not reimbursable under a particular insurance plan. As another example, CCC subsystem 34 may forward information regarding the resolution of clinical alerts to an auditing or compliance subsystem that tracks the use of evidence-based medicine or other policies or regulations. Administrative alerts may be prioritized by Alert Optimizer 38 in the same manner as and/or together with clinical alerts, or administrative alerts may be handled and/or presented separately from clinical alerts.

Alert Optimizer 38 may further adapt a clinical alert by enrichment. An alert may be enriched by modifying the amount of information, the kind of information, and/or the terminology used to convey the alert. The alert may be enriched by focusing the content and terminology for the intended audience of the alert. For example, an alert may be enriched based on the role of the clinician using the system. A potential adverse drug interaction may be initially alerted to the clinician writing the prescription, identifying the drugs involved and generally describing the potential interaction. If overridden or ignored, an alert for the same potential adverse drug interaction may be presented to a pharmacist filling an order for one or more of the medications. The alert for the pharmacist may identify the drugs involved, and present more detailed information regarding the nature and likelihood of the adverse interaction. If overridden or ignored, an alert for the same potential adverse drug interaction may be presented to a pharmacy technician who delivers the medication to the patient. The alert for the medical technician may identify the drugs involved and mention that the patient should call the prescribing clinician if certain symptoms of the possible adverse interaction arise.

The intended audience of the alert may be the current system user. In some circumstances, it may be desirable to enrich an alert for someone other than the current system user. For example, a clerk or transcriptionist who enters data and/or orders into the HIT system for a clinician may not be able to act on the alert, or may merely report the alert back to the clinician who provided the data and/or orders. The Alert Optimizer may enrich the alert for the clinician associated with the data and/or orders, rather than the current system user. The relationship between the clinician and the current system user may be known or inferred, for example, from user profiles, sign-on procedures, or data-entry procedures. In some circumstances, it may be desirable to enrich an alert for a clinician other than the clinician whose data and/or orders triggered the alert. For example, an alert may be enriched for a pharmacist who is tasked with filling an order that triggered an alert, instead of or in addition to enriching the alert for the clinician who initially entered the medication order.

Alert Optimizer 38 may further adapt a clinical alert by formatting the alert for an intended audience. Alert text may be formatted to make it visually distinct from the remainder of the content in the user interface at the time the alert is presented. For example, the alert text may be presented in a different font, a different font size, or a different color from other content in the user interface. Different alerts may also be formatted differently based on content. For example, alerts related to inconsistencies in newly entered data may be formatted differently from alerts related to contraindicated treatments and/or alerts related to possible adverse effects of a particular treatment or combination of treatments, and both may be formatted differently from administrative alerts. As another example, alerts which have been resolved by reconciliation by the Alert Optimizer 38, as by applying a policy rule or patient preference, may be presented in a visually distinct manner from alerts which are pending clinician review and/or alerts which were resolved, ignored, or overridden by a clinician. As another example, alerts of different levels or score ranges may be formatted differently. For example, in a 3-level ranking scale, urgent, precautionary, and advisory alerts may be presented in visually distinct formats. As another example, if a medical scoring system is used, ranges may be applied that correspond to or are separate from a level system, if a level system is used with the medical scoring system. Alerts in different medical score ranges may be presented in visually distinct formats.

Figure 3:
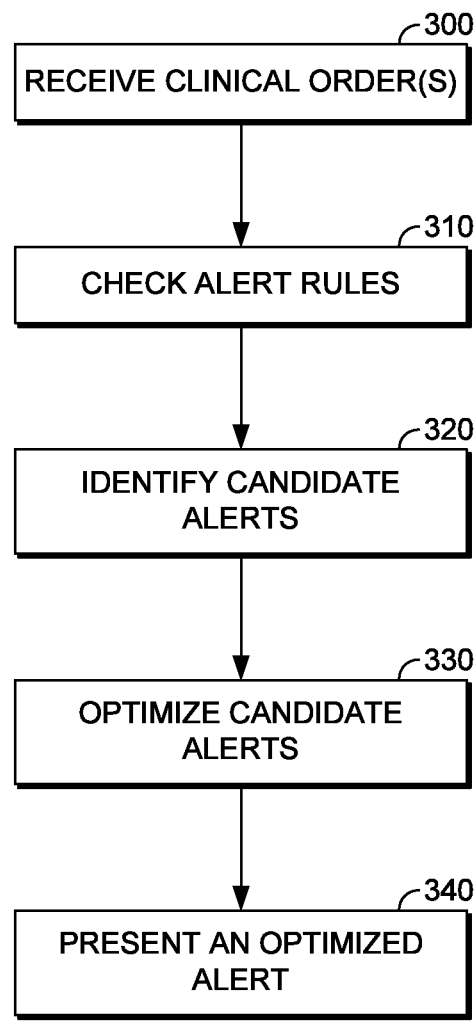
FIG. 3 is a flow chart depicting some aspects of the disclosure.

To optimize an alert, the HIT system may receive one or more clinical orders related to an EHR, shown as step 300 in FIG. 3. The one or more clinical orders may be entered directly into an EHR via an EHR subsystem 30, or may be received by a COE subsystem 32, which may be separate from or a subsystem of the EHR subsystem 30. The clinical orders may be related to any clinical procedure, diagnosis, treatment, follow-up or documented patient counseling (e.g., medical advice, whether related to physical or mental health). The COE subsystem 32 may send the clinical order(s) to CCC subsystem 34 for a clinical conflict check. Alternately, CCC subsystem 34 may call for clinical order(s) from the COE subsystem 32. If CCC subsystem 34 calls for the clinical orders, such a call may be placed at a predetermined time, such as on completion of an order entry form, or on completion of a data entry form for an EHR during a patient encounter.

On receipt of one or more clinical orders or EHR entries, CCC subsystem 34 may call for alert rules 36, shown as step 310 in FIG. 3. Alternately, updates or changes to alert rules 36 may be pushed to the CCC subsystem 34 when the updates or changes are made, or alert rules 36 may be periodically refreshed regardless of whether updates or changes have been made. Depending on the identity of the clinician, the role of the clinician, the nature of the patient encounter, or any other designated criteria, specific alert rules, such as alert rules 36a, 36b, or 36c may be used. Based on alert rules 36 and/or clinical orders, CCC subsystem 34 may call for relevant information from the patient's EHR. Using alert rules 36, CCC subsystem 34 identifies candidate clinical alerts related to the one or more clinical orders in relation to the patient's EHR, shown as step 320 in FIG. 3.

CCC subsystem 34 may comprise an Alert Optimizer subsystem 38 or may send candidate clinical alerts to an Alert Optimizer 38. A separate Alert Optimizer 38 may be useful, for example, but not exclusively, when adding the Alert Optimizer 38 to a pre-existing HIT system 20. Alert Optimizer 38 may optimize candidate alerts, e.g., by filtering, prioritizing, enriching, and/or formatting the candidate alerts, shown as step 330 in FIG. 3. CCC subsystem 34 may transmit situational patient data to Alert Optimizer 38, or Alert Optimizer 38 may separately extract relevant information from the patient's EHR, or both. Situational patient data may include patient demographics, clinical test results, clinical observations, medical conditions, medical risk factors, recent clinical orders, patient medication history, active patient medication, patient home medication, patient allergies, patient diagnosis, patient genetics, prior patient clinical choices, patient clinical directives, or combinations thereof. Patient clinical directives may include general instructions provided by the patient, such as uniformly declining all vaccines, or certain diagnostic procedures, or certain treatments. An EHR may be described as "associated with" the HIT System 20 and/or Alert Optimizer 38 if Alert Optimizer 38 has access to and can read the EHR. An EHR accessible in a HIT system may or may not reside on the same networked computing device or storage media as any other component of the HIT system. In some instances, the EHR may have been initiated and/or may be maintained by a separate organization or entity. For example, two independent regional hospitals may maintain separate HIT systems, but agree to share access to each other's EHRs for continuity of patient care as patients work with clinicians associated with one hospital or the other.

Alert Optimizer 38 may comprise or may access a medical knowledge model to score the candidate clinical alerts based on likelihood of an adverse event, severity of an adverse event, or both. Alert Optimizer 38 may use the score directly, and/or may assign each candidate clinical alert a level. A level system may have at least two levels, such as high priority and low priority. A level system may have at least three levels, such as urgent, precautionary, and advisory. A level system may have four, or five, or six, or more levels, for example, subdividing each or any of the urgent, precautionary, and advisory levels into further stratified levels of importance, likelihood, and/or severity. One of skill in the art will appreciate that the precise labels used for each level is not necessarily important, as long as the labels are useful for distinguishing the clinical significance of alerts in the different levels. For example, an urgent alert might also be described as high priority, high relevancy, high impact, important, critical, etc.

HIT System 20 may include a database of prior alerts. The database of prior alerts may be associated with EHR subsystem 30, COE subsystem 32, CCC subsystem 34, or may be maintained as a separate component of HIT System 20. Alert Optimizer 38 may access the database of prior alerts for a given patient. Alert Optimizer 38 may filter out alerts which were previously presented and ignored or overridden by the clinician who issued the most recent orders related to the patient. The filtered-out alerts may not be presented to the clinician again, since they have previously been ignored or overridden for a particular patient. Alert Optimizer 38 may further consider whether an alert is inconsistent with patient situational data, such as patient medication history, active patient medication, and/or patient home medication. For example, a potential adverse drug interaction alert may be filtered out if the patient has previously taken the same combination of medications without experiencing the adverse interaction, or has tolerated any adverse interaction well. Alert Optimizer 38 may filter out any alert inconsistent with a patient care directive or prior patient clinical choice. For example, Alert Optimizer 38 may filter out alerts related to an overdue mammogram for a patient who has routinely declined mammography. Alert Optimizer 38 may act on a single prior patient clinical choice, or may look for a repeated patient clinical choice, such as refusing a particular procedure on 2 consecutive occasions, or 3 consecutive occasions, or 4 consecutive occasions, or 5 or more consecutive occasions.

Alert Optimizer 38 may address alert fatigue by reducing the number of alerts presented. That is, even if no candidate alerts are filtered out for other reasons, Alert Optimizer 38 may deselect for presentation alerts beyond a threshold number, such as 5, 10, 15, 20, etc. alerts. Alert Optimizer 38 may prioritize for presentation alerts with a certain medical score or level. Alert Optimizer 38 may, for example, withhold from presentation advisory alerts if a total number of optimized alerts exceeds a threshold number. If a total number of optimized alerts exceeds a second threshold number, Alert Optimizer 38 may withhold from presentation precautionary clinical alerts, or precautionary clinical alerts with a medical score below a predetermined cutoff value. Alerts withheld from presentation may still be accessible by the clinician, e.g., in a particular section or tab of a graphical user interface, or may not be presented at all. If desired, filtered-out alerts could be presented in a visually distinct formatting that de-emphasizes the filtered-out alerts relative to optimized alerts. For example, filtered-out alerts may be presented in a smaller font, with less contrast with the surrounding content, and/or in a less prominent position in a graphical user interface or record print-out than optimized alerts.

In some instances, alert rules 36 may include prescribed resolutions to certain alerts. For example, a healthcare delivery organization may adopt a policy forbidding the administration of a particular combination of drugs, or requiring a consultation with a specialist before a certain treatment is ordered, or requiring that a mammogram be offered even if such an offer seems unnecessary in view of prior patient clinical choices or patient care directives. Alert Optimizer 38 may apply a prescribed resolution automatically. Alert Optimizer 38 may present the alert with the resolution, with other alerts or separately, e.g., in a separate section or tab in a graphical user interface. Alert Optimizer 38 may enhance automatically resolved alerts by changing the text and/or formatting of the alert. For example, the text of an automatically resolved alert may begin with a description of the change to the orders, followed by the reason. As another example, automatically resolved alerts may be presented in a manner which is visually distinctive from alerts pending clinician review, and/or alerts which were resolved, ignored, or overridden by the clinician.

Optimized clinical alerts may be presented, or rendered for presentation, to a human system user, shown as step 340 in FIG. 3. The presentation may involve a graphical user interface that provides an overview of alerts related to a particular record or order, with the option to get additional information about the alert, e.g., by clicking on a brief description of the alert. Upon presentation, a human system user may have the option to modify the clinical order and/or EHR entry that prompted the alert, ignore the alert, or override the alert (e.g., affirmatively acknowledge the alert and proceed with the order which triggered the alert). If an alert is overridden, the system may provide an opportunity for the clinician to add a note regarding the reason for overriding the alert. Alternately, or in addition to presenting the alerts in a cumulative overview, individual alerts may be presented, e.g., as pop-up windows or click-through screens, for clinician review. HIT system 20 may record the presentation of alerts. HIT system 20 may record the response, if any, to a presented alert. Candidate alerts which were withheld or suppressed may be viewable in a special interface (e.g., through clicking a link to "Other Alerts"), or may be entirely suppressed or withheld (e.g., not made available or visible to the clinician).

In some aspects, Alert Optimizer 38 may improve a human-user interface for clinical alerts in a HIT system 20. HIT system 20 may access a patient's EHR, shown as step 400 in FIG. 4. HIT system 20 may apply a medical knowledge model to determine a clinical situation from the patient's EHR, shown as step 410 in FIG. 4. For example, HIT system 20 may assess recent complaints, diagnoses, prognoses, patient encounters, etc. to evaluate a patient's current condition and likely treatment and/or follow-up plan. HIT system 20 may apply a set of clinical alert rules to the patient's EHR, shown as step 420 in FIG. 4. The clinical alert rules may be applied based on the clinical situation and/or different clinical alert rules may be applied for different clinical situations. For example, different clinical alert rules may be used for in-patient healthcare than for out-patient healthcare, or for patients with different diagnosed conditions, e.g., generally well/no current condition, heart disease, diabetes, etc.

Figure 4:
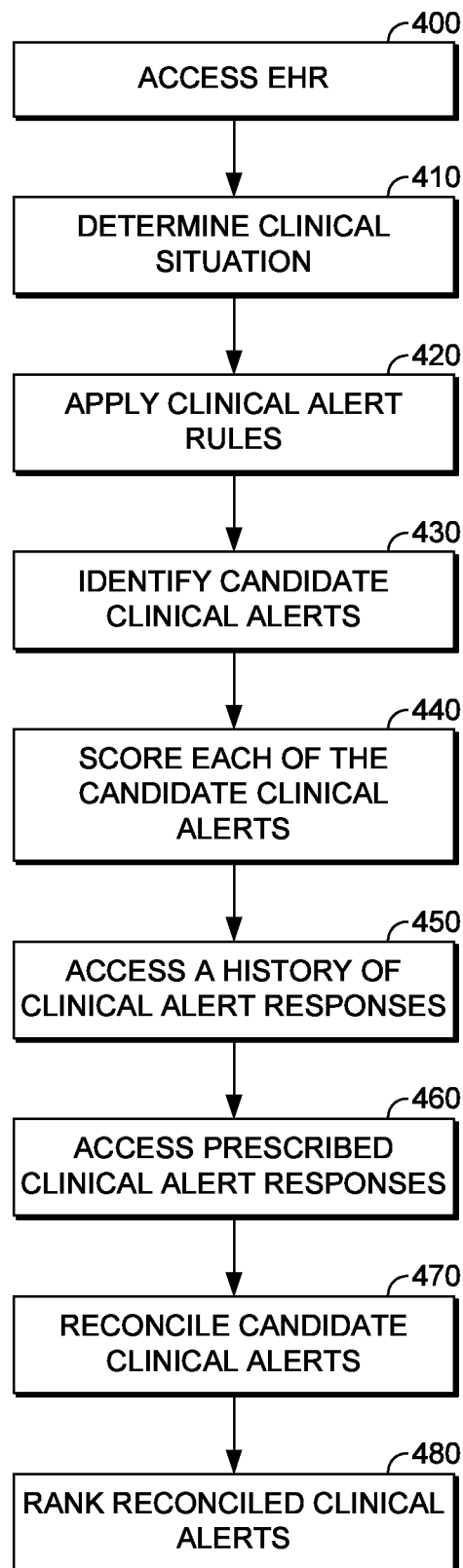
FIG. 4 is a flow chart depicting some aspects of the disclosure.

By applying the clinical alert rules, one or more candidate clinical alerts applicable to the patient's EHR may be identified, shown as step 430 in FIG. 4. The HIT system may score each of the one or more candidate clinical alerts applicable to the patient's EHR based on the likelihood and/or severity of an undesirable outcome related to the clinical alert, shown as step 440 in FIG. 4. The HIT system may use the clinical situation, the medical knowledge model, and/or information from the EHR to score the candidate clinical alerts. As an example, a candidate clinical alert may receive a high (undesirable) score if an undesired outcome associated with the conditions that triggered the alert is both severe and likely. Likelihood may be assessed at least in part based on whether the patient in question has ever been exposed to the conditions that triggered the alert, and, if so, whether the patient experienced the undesired outcome. For example, some adverse drug reactions are not uniformly experienced by all patients, or the severity of the reaction is not uniform among patients. If a particular patient has taken the particular medicine in the past without any ill effect, and the clinical situation has not changed in a relevant way, the score may be lower for that particular patient than for other patients. Conversely, if a patient has taken the particular medicine in the past and was shortly afterwards treated for anaphylaxis, the score may be higher for that particular patient than for other patients. The scoring may provide or may be used to generate different bands or levels of alerts. That is, rather than an abstract number as a score, the score may be converted to levels such as urgent, precautionary, and advisory.

HIT system 20 may access a history of past clinical alert responses associated with the patient, shown as step 450 in FIG. 4. The history may include how the alerts were resolved. Alerts which were intentionally overridden by the same clinician under similar clinical circumstances may be handled with less urgency than alerts which resulted in changed orders from the same clinician in the past. Similarly, alerts which were overridden with notes regarding patient preferences or directives may be handled with less urgency than alerts which were ignored without comment or resolution.

HIT system 20 may access a list of prescribed clinical alert responses, shown as step 460 in FIG. 4. For example, a particular healthcare organization may have policies or procedures in place that require a clinical alert to be resolved in a particular way, or that trigger an alert that the organization does not wish to enable the clinician to override. Such alerts may, for example, be related to evidence-based best practices, policy choices made by the organization, legal or regulatory requirements, or risk management practices of the organization. The prescribed clinical alert responses may require that an order not be accepted until modified to be in compliance with the policy or procedure, or may automatically modify the order to make it comply with the policy or procedure.

HIT system 20, for example, through Alert Optimizer 38, may reconcile the candidate clinical alerts for a particular patient in a particular clinical situation, shown as step 470 in FIG. 4. Alert Optimizer 38 may reconcile the candidate clinical alerts using, at least in part, the past clinical alert responses and/or the prescribed clinical alert responses. This reconciliation may involve adding, deleting, or changing one or more candidate clinical results. For example, a clinical alert related to an adverse drug reaction may be modified or deleted if the facility's policy is to not prescribe that particular drug without concurrence from a second clinician. In this way, the clinician ordering the drug is not shown two separate alerts, one for the policy exception and one for the potential adverse reaction, but is instead shown the primary alert, which may be the facility rule preventing the order from being entered. The text of the alert may be modified to include or reference the potential adverse event, or the information regarding the potential adverse event may be suppressed as less relevant since the medication cannot be ordered immediately. The reconciliation process may sometimes result in the addition of an alert. For example, if a child is to be admitted to a chronic care program that requires measles vaccines, and has not been vaccinated, in addition to an alert about the unfulfilled entrance requirement, the system may present an alert related to a patient care directive declining all vaccinations. As another example, the reconciliation process may identify conflicting recommendations in different alerts. In such a case, the reconciliation process may involve considering the clinical situation to determine, with reference to the medical knowledge model, which recommendation is likely to be most beneficial. The reconciliation process may involve suppressing the alert containing the least beneficial recommendation. As still another example, the reconciliation process may involve suppressing alerts which, if acted upon (i.e., if the orders were changed as suggested by the alert), would result in a different alert (e.g., an "alert loop"). For example, if the evidence-based best practice for a given infection is the administration of penicillin, but the patient is allergic to penicillin, the reconciliation process may suppress or withhold an alert recommending that an order for cephalexin (an alternative antibiotic) be changed to penicillin.

After the candidate clinical alerts have been reconciled, the reconciled clinical alerts (of which there may be more or fewer alerts than there were candidate clinical alert results) may be ranked based, for example, on score, past or prescribed alert responses, and/or the clinical situation, shown as step 480 in FIG. 4. All of the reconciled clinical alerts may be presented to a human system user. If a high number of reconciled clinical alerts are generated, e.g., more than 5, or 10, or 15, or 20, or more, the HIT system may not present all of the reconciled clinical alerts. The most highly ranked clinical alerts may be presented to a human system user, e.g., as a percentile based on the scores of the body of reconciled clinical alerts. If a threshold number of reconciled clinical alerts are generated, the HIT system may not present reconciled clinical alerts of an advisory nature. If a second threshold number of reconciled clinical alerts are generated, the HIT system may not present reconciled clinical alerts of a precautionary nature. The HIT system may present all urgent alerts, or all alerts above a designated medical score, or all alerts above a designated likelihood score, or all alerts above a designated severity score. If the urgent alerts do not reach the threshold number of alerts for suppressing advisory and/or precautionary alerts (in systems which suppress such alerts), precautionary and/or advisory alerts may be presented only until a threshold number of clinical alerts have been presented. The HIT system may present all novel alerts and/or alerts which resulted in changed orders in the past, suppressing alerts which have been overridden or ignored in the past. Whichever reconciled alerts are presented, they may be presented in ranked order, such that the most relevant and important alerts are presented first.

The methods and systems described provide processing advantages at least in part because the processing can be handled centrally, e.g., by the computing device which serves to store the HIT system 20 and/or process transactions for the HIT system 20. The number of alerts presented (and, correspondingly, responses received) will generally decrease with optimized and/or reconciled results. This reduces the time required to render human-readable alert presentations, as well as the communication bandwidth to communicate various alerts and responses between different networked computing and/or storage devices. At a minimum, the optimized and/or reconciled results redirect processing capacity and communication bandwidth to the handling of alerts that have been pre-screened for relevancy and importance. Using an Alert Optimizer also reduces the time required for a clinician to review results, and, where the results are fewer in number and/or of greater relevance, may reduce so-called "alert fatigue". The interface between the HIT system and a human system user may be improved by, for example, providing more relevant, more important, and/or enriched alerts, which allows the user to reduce the attention devoted to interacting with the HIT system during and/or after a patient encounter.

Technology for consulting, referencing, or otherwise identifying useful information in an EHR or medical knowledge database may take many forms, and continues to evolve. Exemplary means for electronically searching an EHR may rely on standards such as Clinical Document Architecture (CDA), Continuity of Care Document (CCD), or Continuity of Care Record (CCR). These standards may be sufficient, particularly, but not exclusively, when a patients' caregivers use the same HIT System 20, use the same kind of HIT System 20, use the same health information documentation standards, or otherwise are compatible for the purpose of automated searching and interpretation of the records. Other exemplary means for identifying, e.g., complaints, diagnoses, conditions, allergies, etc. from a EHR include automated ontology mapping, as described, for example, in U.S. Pat. No. 8,856,156, which is incorporated by reference in its entirety.

An exemplary structure for searching an EHR may provide access to one or more EHR systems communicatively coupled to a network. The structure may include software for retrieving items, records, and data values from a particular record or from all of the records. Suitable software may include the commercially available "R system", software for latent semantic analysis (LSA), data mining software such as that available from WEKA, software utilizing Quinlan algorithms, software utilizing cosine and Pearson correlation, software using decision tree classification, comparable techniques or algorithms, or combinations thereof. A particular EHR may be mined in advance of need from a CCC or alert optimizer, e.g., with potentially useful data stored in a database apart from the EHR itself, or may be mined upon the need of particular information from the EHR. The mined data may be examined for shared codes, such as diagnostic or billing codes, that provide relevant information; or may be mined for key words, preferably with the benefit of contextual analysis. In some HIT Systems, cover sheets, case reports, or data summaries may be saved or prepared to facilitate mining for particular data, such as diagnoses, latest complaint(s) or symptoms, current medications, recent test results, recent examination findings, and combinations thereof.

EXAMPLE 1

Situation: Patient has a documented penicillin allergy with reaction type Anaphylaxis.

Case 1: Clinician orders penicillin. Both a conventional CCC and the Alert Optimizer return a high level alert related to the patient's penicillin allergy.

Case 2: Clinician orders cephalexin. A conventional CCC still generates a high level alert because of the potential cross-reactivity reaction between penicillins and cephalosporins (i.e., the prior allergic reaction to penicillin makes it more likely that the patient will have an allergic reaction to cephalosporins than if the patient did not have a history of allergic reaction to penicillin).

The Alert Optimizer consults a medical knowledge model and recognizes that penicillin has a drug class of Natural Penicillins/Antibiotic and Cephalexin has a drug class of Cephalosporin/Antibiotic. The Alert Optimizer further recognizes that the patient previously had a hypersensitivity reaction to Doripenem, a drug that belongs to the class of Carbapenem/Antibiotic. Drugs from Cephalosporin and Carbapenem classes may cause cross allergic reactions in patients allergic to penicillin. The reaction to Doripenem manifested as erythematous maculopapular eruption on the trunk and extremities, starting on the last day of medication therapy. The reaction to Doripenem resolved after the administration of a single 25 mg dose of antihistamine (Diphenhydramine). The probability of a cross-reaction to Cephalexin may be slightly increased due to the patient's recent history of the hypersensitivity reaction to Doripenem and the potential for cross allergic reactions between Cephalosporins and Carbapenems. However, the lesser severity of the reaction to Doripenem and the prompt resolution on administration of antihistamine cause the Alert Optimizer to deprioritize this alert to a medium-low or precautionary level.

EXAMPLE 2

Situation: Patient has a documented penicillin allergy with reaction type Eye Irritation.

Case 1: Clinician orders penicillin. A conventional CCC generates a high level alert related to the patient's penicillin sensitivity. The Alert Optimizer deprioritizes this alert to a precautionary or advisory alert (minor risk) due to the less severe outcome, as compared to anaphylaxis in Example 1.

Case 2: Clinician orders cephalexin. A conventional CCC still generates a high level alert related to the patient's penicillin sensitivity.

The Alert Optimizer consults a medical knowledge model and recognizes that penicillin has a drug class of Natural Penicillins/Antibiotic. The Alert Optimizer further recognizes that Cephalexin has a drug class of Cephalosporin/Antibiotic. The Alert Optimizer deprioritizes this alert to a minor level due to the less severe reaction (slight hypersensitivity vs. anaphylaxis) and because this medication belongs to a different drug class with a remote probability of cross-sensitivity reactions, reducing the likelihood of an adverse reaction.

EXAMPLE 3

A physician is treating an African-American female, 67 years old. In this hypothetical treatment scenario, the patient has a history of Hypertension NOS, Diabetes Mellitus (I9CDXI250.00), and Asthma. The patient was diagnosed with pruritus last week. Her last asthma attack was 6 months ago. Patient complains of constipation.

The physician proposes refilling prior prescriptions for an Albuterol rescue inhaler and Hydroxyzine. The patient is actively taking Hydroxyzine, 25 mg 4 times per day for 5 days; Albuterol as needed; Aspirin; Diltiazem; Glimepiride; Hydrochlorothiazide; Losartan; Metformin; and Sitagliptin.

Patient test results and findings for Body Mass Index (BMI), temperature, respiration rate, and systolic blood pressure are all normal. Potassium levels are on the low end of the normal range. An electrocardiogram shows QTc prolongation.

On placing orders for the refill medications into a Clinical Order Entry (COE system), a Clinical Conflict Check (CCC system) generates the following Drug-Drug Interaction Alerts, where code B indicates that no action is needed; code C recommends monitoring the therapy; and code D recommends therapy modification:

[D] Glimepiride (Sulfonylureas)—Sitagliptin (DPP-IV Inhibitors)
[C] Aspirin (Salicylates)—Diltiazem (Calcium Channel Blockers (Nondihydropyridine))
[C] Aspirin (Salicylates)—Glimepiride (Blood Glucose Lowering Agents)
[C] Aspirin (Salicylates)—Metformin (Blood Glucose Lowering Agents)
[C] Aspirin (Salicylates)—Sitagliptin (Blood Glucose Lowering Agents)
[C] Diltiazem (Antihypertensives)—Hydrochlorothiazide (Antihypertensives)
[C] Diltiazem (Antihypertensives)—Losartan (Antihypertensives)
[C] Diltiazem (Hypotensive Agents)—Hydrochlorothiazide (Hypotensive Agents)
[C] Diltiazem (Hypotensive Agents)—Losartan (Hypotensive Agents)
[C] Glimepiride (Antidiabetic Agents)—Hydrochlorothiazide (Hyperglycemia-Associated Agents)
[C] Glimepiride (Antidiabetic Agents)—Hydrochlorothiazide (Thiazide Diuretics)
[C] Glimepiride (CYP2C9 Substrates)—Losartan (CYP2C9 Inhibitors (Moderate))
[C] Glimepiride (Hypoglycemia-Associated Agents)—Metformin (Antidiabetic Agents)
[C] Albuterol (Beta2-Agonists)—Hydrochlorothiazide (Thiazide Diuretics)
[C] Hydrochlorothiazide (Antihypertensives)—Losartan (Antihypertensives)
[C] Hydrochlorothiazide (Hyperglycemia-Associated Agents)—Metformin (Antidiabetic Agents)
[C] Hydrochlorothiazide (Hyperglycemia-Associated Agents)—Sitagliptin (Antidiabetic Agents)
[C] Hydrochlorothiazide (Hypotensive Agents)—Losartan (Hypotensive Agents)
[C] Hydrochlorothiazide (Thiazide Diuretics)—Hydroxyzine (Anticholinergic Agents)
[C] Hydrochlorothiazide (Thiazide Diuretics)—Metformin (Antidiabetic Agents)
[C] Hydrochlorothiazide (Thiazide Diuretics)—Sitagliptin (Antidiabetic Agents)
[B] Albuterol (QTc-Prolonging Agents (Indeterminate Risk and Risk Modifying))—Hydroxyzine (QTc-Prolonging Agents (Indeterminate Risk and Risk Modifying))

An Alert Optimizer System according to the present invention is activated. Using a medical knowledge (classification) model and an inferencing engine, the Alert Optimizer classifies all available clinical alerts (which may include the drug-drug interaction alerts above as well as other clinical alerts, depending on the scope and capabilities of the CCC system). Alert risk is classified for each clinical alert. In this example, the risk classification system has four levels: High for life threatening situations; Moderate for potentially harmful situations; Medium-Low for situations with somewhat lower potential for harm; and Minor for situations that pose a remote probability of harm.

The Alert Optimizer consults the Medical Knowledge model, looking for relationships between the test results and examination findings, known problems/conditions/complaints, the proposed medications, the role of the clinician triggering the alert optimization (in this case, a physician), and Anatomical Therapeutic Chemical (ATC) classifications (as maintained by the World Health Organization or a comparable classification system). As an example, because the patient has been diagnosed with diabetes, the Medical Knowledge model suggests particular care in prescribing drugs which may cause hyperglycemia or hypoglycemia. Of the proposed medications, the thiazide diuretics hydroxyzine and sitagliptin are identified as potential triggers of hyperglycemia and/or hypoglycemia.

The Alert Optimizer uses the inferencing engine to process a set of alert risk rules, which may be customized for a particular practitioner, institution, healthcare network, etc. Exemplary rules include the following:

| Alert Risk Class | Rule |
| --- | --- |
| High (Life Threating Situation) | Any Clinical Alert and (Med1 partOf (A10BA Biguanides) or Med2 partOf (A10BA Biguanides)) and hasPatientDiagnosis Acute Kidney Failure |
| Moderate (Potentially Harmful) | Any Clinical Alert and hasPatientResult = ECG hasValue = Abnormal and hasQtProlongation AboveNormalRange and Med1 = Albuterol and Med2 = Hydroxyzine |
| Medium-Low (Potential for Harm) | Any Clinical Alert and Med1 partOf (Thiazide Diuretics) and Med2 partOf (A10B Blood glucose lowering drugs, excluding insulins) |
| Minor (Remote Probability for Harm) | Any Clinical Alert and Med1 and Med2 partOf (A10B Blood glucose lowering drugs, excluding |

| Alert Risk Class | Rule |
| --- | --- |
| | insulins) and hasPatientDiagnosis Diabetes Mellitus and hasResult Blood Glucose hasValue High or Normal |

In this exemplary embodiment, the model and rules are described using Web Ontology Language (OWL).
The Drug-Drug Interaction alerts described above are classified as follows:
High (Life Threating Situation)
  None
Moderate (Potentially Harmful)
  Albuterol (QTc-Prolonging Agents (Indeterminate Risk and Risk Modifying))
  Hydroxyzine (QTc-Prolonging Agents (Indeterminate Risk and Risk Modifying))
Low (Potential for Harm)
  Glimepiride (Antidiabetic Agents)—Hydrochlorothiazide (Thiazide Diuretics)
  Glimepiride (Sulfonylureas)—Sitagliptin (DPP-IV Inhibitors)
  Glimepiride (CYP2C9 Substrates)—Losartan (CYP2C9 Inhibitors (Moderate))
Minor (Remote Probability for Harm)
  Glimepiride (Hypoglycemia-Associated Agents)—Metformin (Antidiabetic Agents)
  Aspirin (Salicylates)—Diltiazem (Calcium Channel Blockers (Nondihydropyridine))
  Aspirin (Salicylates)—Glimepiride (Blood Glucose Lowering Agents)
  Aspirin (Salicylates)—Metformin (Blood Glucose Lowering Agents)
  Aspirin (Salicylates)—Sitagliptin (Blood Glucose Lowering Agents)

Depending upon the total number of clinical alerts identified, the relative ranking of the clinical alerts, and the preferences programmed into the system (e.g., total number of alerts to be displayed and/or format to be used for alerts of different alert risk classifications), the identified clinical alerts are ordered, formatted, and presented to the physician for review. Because the user was identified as the prescribing physician, the alerts may be modified to present alternate dosing, medication, or treatment information; recommended orders for monitoring therapy; and/or the like, suitable to the prescribing physician's role.

From the foregoing, it will be seen that the concepts described are well adapted to attain all the ends and objects hereinabove set forth together with other advantages which will be appreciated by those of skill in the art from reading this disclosure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

Having thus described the invention, what is claimed is:

1. A method for preserving computer processing capacity in a Health Information Technology (HIT) system, the method comprising:
  receiving one or more clinical orders from a clinician, the one or more clinical orders specific to a patient;
  checking the one or more clinical orders against a set of clinical alert rules;
  identifying two or more candidate clinical alerts related to the clinical orders and the set of clinical alert rules;
  optimizing the two or more candidate clinical alerts to create an optimized clinical alert, the optimizing comprising:
    accessing a patient-specific alert history and a patient-specific Electronic Health Record (EHR), the patient-specific alert history comprising a past clinical alert associated with the patient and an indication that the clinician overrode the past clinical alert, wherein the past clinical alert was overridden prior to receiving the one or more clinical orders from the clinician;
    identifying a first clinical condition associated with the past clinical alert;
    identifying a second clinical condition associated with a first candidate clinical alert of the two or more clinical candidate alerts;
    determining that the first clinical condition associated with the past clinical alert is the same as the second clinical condition associated with the first candidate clinical alert; and
    filtering out the first candidate clinical alert such that the first candidate clinical alert is not presented to the clinician on a user interface of a clinician device; and
  presenting the optimized clinical alert, for display by the user interface of the clinician device, wherein the optimizing reduces processing capacity required to present the candidate clinical alerts.

2. The method of claim 1, wherein checking the clinical alert rules comprises:
  identifying clinical information relevant to checking the clinical alert rules;
  accessing the EHR associated with the HIT system; and
  extracting the relevant clinical information from the EHR.

3. The method of claim 2, wherein the relevant clinical information comprises patient demographics, clinical test results, clinical observations, medical conditions, medical risk factors, recent clinical orders, patient medication history, active patient medication, patient home medication, patient allergies, patient diagnosis, patient genetics, prior patient clinical choices, patient clinical directives, or combinations thereof.

4. The method of claim 3, wherein optimizing the two or more clinical alerts comprises filtering out a second candidate clinical alert of the two or more candidate clinical alerts, wherein the second candidate clinical alert is inconsistent with the patient medication history, active patient medication, and/or patient home medication, such that the second candidate clinical alert is not presented.

5. The method of claim 3, wherein optimizing the two or more clinical alerts comprises filtering out a second candidate clinical alert of the two or more candidate clinical alerts, wherein the second candidate clinical alert is inconsistent with a patient care directive or prior patient clinical choice, such that the second candidate clinical alert is not presented.

6. The method of claim 1, further comprising assigning to each candidate clinical alert of the two or more candidate clinical alerts a level based on a likelihood of an undesired outcome and a severity of the undesired outcome.

7. The method of claim 6, wherein the level distinguishes at least between urgent, precautionary, and advisory clinical alerts.

8. The method of claim 7, wherein if a total number of optimized alerts exceeds a threshold number, advisory clinical alerts are not presented.

9. The method of claim 8, wherein if the total number of optimized alerts exceeds a second threshold number, precautionary clinical alerts are not presented.

10. The method of claim 1, further comprising generating alert text targeted to a variable audience.

11. The method of claim 10, wherein the variable audience is defined by a role of a system user.

12. The method of claim 11, further comprising formatting an alert targeted to the system user.

13. The method of claim 10, wherein the variable audience is defined by a role of a clinician who generated the clinical order underlying the optimized clinical alert.

14. The method of claim 13, further comprising formatting an alert targeted to the clinician.

15. The method of claim 1, further comprising:
   accessing a prescribed actions list; and
      filtering out any alert which has a prescribed resolution, such that the first candidate clinical alert is not presented.

* * * * *